(12) United States Patent
Clark (10) Patent No.: US 9,872,932 B2
(45) Date of Patent: Jan. 23, 2018

(54) FRUIT AND CLOVE POMANDER KIT

(71) Applicant: Teresa Maureen Clark, Rogers, AR (US)

(72) Inventor: Teresa Maureen Clark, Rogers, AR (US)

( * ) Notice: Subject to any disclaimer, the term of this patent is extended or adjusted under 35 U.S.C. 154(b) by 241 days.

(21) Appl. No.: 14/753,863

(22) Filed: Jun. 29, 2015

(65) Prior Publication Data

US 2016/0030619 A1 Feb. 4, 2016

Related U.S. Application Data

(60) Provisional application No. 62/030,264, filed on Jul. 29, 2014.

(51) Int. Cl.
| | | |
|---|---|---|
| *A61L 9/12* | (2006.01) | |
| *B26D 9/00* | (2006.01) | |
| *B26B 27/00* | (2006.01) | |
| *A61L 9/013* | (2006.01) | |
| *B26F 1/32* | (2006.01) | |
| *A61L 2/00* | (2006.01) | |
| *A61L 9/00* | (2006.01) | |
| *B65D 33/04* | (2006.01) | |
| *B65D 33/14* | (2006.01) | |

(52) U.S. Cl.
CPC ...... *A61L 9/12* (2013.01); *A61L 2/00* (2013.01); *A61L 9/00* (2013.01); *A61L 9/013* (2013.01); *B26B 27/00* (2013.01); *B26D 9/00* (2013.01); *B26F 1/32* (2013.01); *B65D 33/04* (2013.01); *B65D 33/14* (2013.01)

(58) Field of Classification Search
CPC . B26F 1/32; B65B 27/00; A61L 19/00; A61L 19/12; A61L 19/013; A61L 2/00; A61L 9/12; A61L 9/013; A61L 9/00; B65D 25/10; B65D 85/70; B65D 9/00; B65D 11/20; B65D 11/00; B65D 2221/00; B65D 15/08; B65D 33/04; B65D 33/14; A45J 25/00; B26D 9/00; B26B 27/00
USPC ............ 206/575, 254, 576, 307.1; 220/751; 29/418; 30/123.7
See application file for complete search history.

(56) References Cited

U.S. PATENT DOCUMENTS

| | | | | |
|---|---|---|---|---|
| 903,067 | A * | 11/1908 | Engman | ............... F21V 35/00 |
| | | | | 248/302 |
| 3,804,450 | A * | 4/1974 | Guenzel | ............... A01B 1/20 |
| | | | | 294/180 |
| 4,083,107 | A | 4/1978 | Kuka | |
| 4,828,114 | A * | 5/1989 | Bardeen | ............. B23D 49/11 |
| | | | | 206/232 |

(Continued)

*Primary Examiner* — King M Chu
*Assistant Examiner* — James M Van Buskirk
(74) *Attorney, Agent, or Firm* — Neustel Law Offices (57) ABSTRACT

A fruit and clove pomander kit for efficiently creating a pomander using fruit and cloves. The fruit and clove pomander kit includes a carving and piercing tool having a piercing end adapted to create pierced holes within a fruit and a carving end opposite of the piercing end. The kit further includes a plurality of dried cloves, a rubber band, a writing instrument and at least one hanger hook. The hanger hook is comprised of a helical portion, an engaging portion extending upwardly from the helical portion and an end portion extending downwardly from the helical portion opposite of the engaging portion. The end user uses the kit to create a pomander with a piece of fruit.

2 Claims, 12 Drawing Sheets

(56) References Cited

U.S. PATENT DOCUMENTS

| | | | |
|---|---|---|---|
| 5,514,022 A * | 5/1996 | Harris | A63H 27/10 |
| | | | 40/214 |
| 5,590,911 A * | 1/1997 | Wilson | B42F 13/40 |
| | | | 283/36 |
| D407,001 S | 3/1999 | Allison | |
| 6,360,442 B2 | 3/2002 | O'Brien | |
| 7,549,228 B2 | 6/2009 | Panopoulos | |
| 2003/0234205 A1 | 12/2003 | McGuyer | |
| 2005/0274242 A1 | 12/2005 | McMahon | |
| 2006/0019002 A1 * | 1/2006 | Xue | A23B 7/148 |
| | | | 426/326 |
| 2010/0108561 A1 | 5/2010 | Bramhall | |

\* cited by examiner

FRUIT AND CLOVE POMANDER KIT

CROSS REFERENCE TO RELATED APPLICATIONS

I hereby claim benefit under Title 35, United States Code, Section 119(e) of U.S. provisional patent application Ser. No. 62/030,264 filed Jul. 29, 2014. The 62/030,264 application is currently pending. The 62/030,264 application is hereby incorporated by reference into this application.

STATEMENT REGARDING FEDERALLY SPONSORED RESEARCH OR DEVELOPMENT

Not applicable to this application.

BACKGROUND OF THE INVENTION

Field of the Invention

The present invention relates generally to a pomander and more specifically it relates to a fruit and clove pomander kit for efficiently creating a pomander using fruit and cloves.

Description of the Related Art

Any discussion of the related art throughout the specification should in no way be considered as an admission that such related art is widely known or forms part of common general knowledge in the field.

A pomander is a ball made from perfumes. In the late Middle Ages through the 17th century, pomanders were worn or carried in a vase as a protection against infection or merely as an article to modify bad smells. Globular cases contained the pomanders and were hung around the neck with a chain or belt.

Modern pomanders are comprised of a fruit (e.g. orange, apple) covered with whole dried cloves to provide a pleasant scent. Modern pomanders using fruit and cloves are cure dried and may last several years. Modern pomanders may be used for perfuming and freshening the air or keeping drawers of clothing and linens fresh, pleasant-smelling and moth-free.

The main problem with modern pomanders is they can be time consuming to make by the end user. Another problem with modern pomanders is that the end user typically does not have all of the tools required to effectively make a fruit and clove pomander.

Because of the inherent problems with the related art, there is a need for a new and improved fruit and clove pomander kit for efficiently creating a pomander using fruit and cloves.

BRIEF SUMMARY OF THE INVENTION

The invention generally relates to a pomander kit which includes a carving and piercing tool having a piercing end adapted to create pierced holes within a fruit and a carving end opposite of the piercing end. The kit further includes a plurality of dried cloves, a rubber band, a writing instrument and at least one hanger hook. The hanger hook is comprised of a helical portion, an engaging portion extending upwardly from the helical portion and an end portion extending downwardly from the helical portion opposite of the engaging portion. The end user uses the kit to create a pomander with a piece of fruit.

There has thus been outlined, rather broadly, some of the features of the invention in order that the detailed description thereof may be better understood, and in order that the present contribution to the art may be better appreciated.

There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview.

Turning now descriptively to the drawings, in which similar reference characters denote similar elements throughout the several views, FIGS. 1 through 5d illustrate a fruit and clove pomander kit 10, which comprises a carving and piercing tool 60 having a piercing end 62 adapted to create pierced holes 16 within a fruit 12 and a carving end 64 opposite of the piercing end 62. The kit further includes a plurality of dried cloves 70, a rubber band 40, a writing instrument 50 and at least one hanger hook 80. The hanger hook 80 is comprised of a helical portion 86, an engaging portion 88 extending upwardly from the helical portion 86 and an end portion 84 extending downwardly from the helical portion 86 opposite of the engaging portion 88. The end user uses the kit to create a pomander with a piece of fruit 12.

B. Main Packaging.

Figure 1:
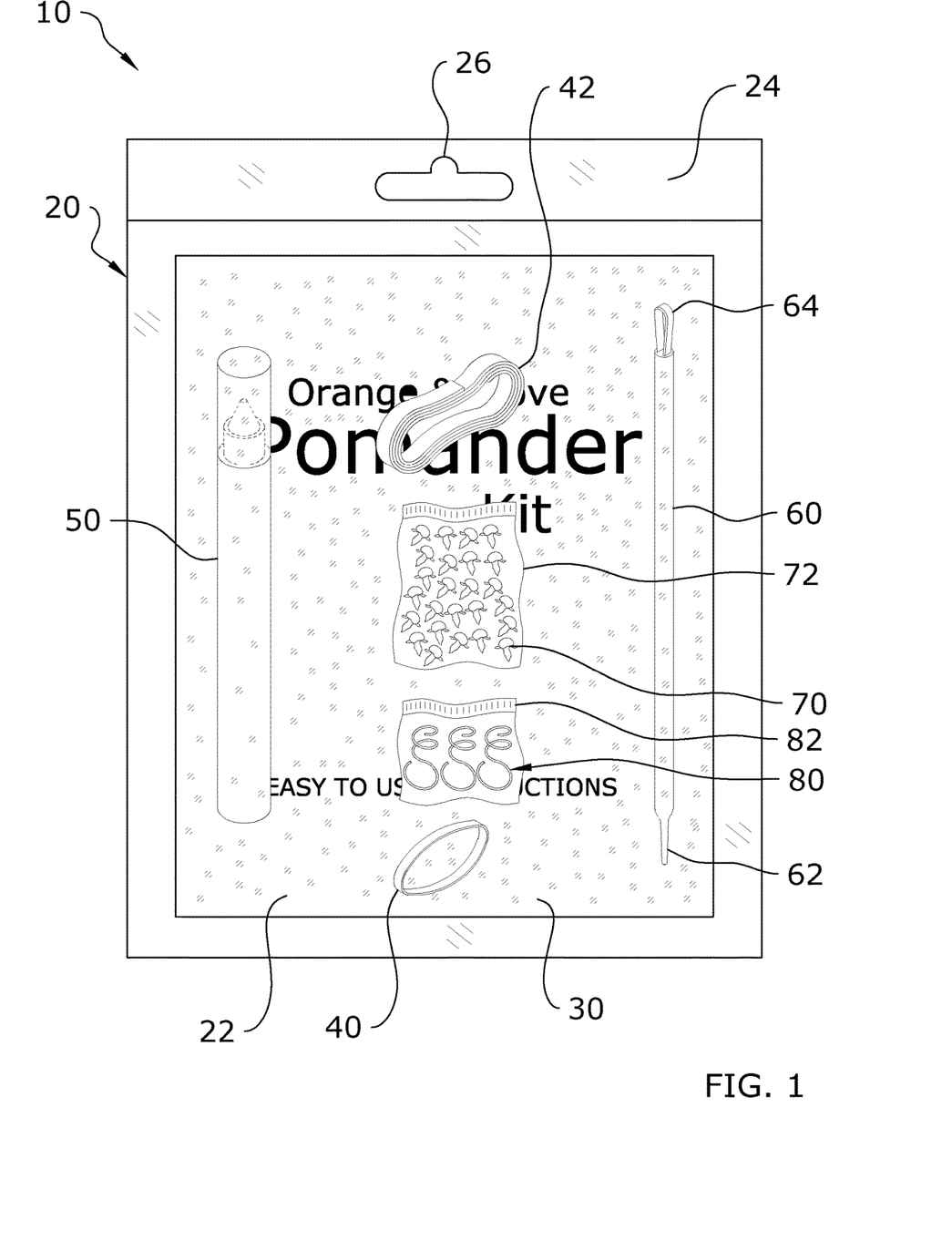
FIG. 1 is an upper perspective view of the present invention in kit form within the main packaging.

The present invention preferably includes a main packaging 20 having an interior cavity that stores the various components of the kit 10. The main packaging 20 is illustrated in FIG. 1 as having a rectangular shaped flattened box structure, however, the main packaging 20 may have various other shapes (e.g. cubed shape, spherical shaped, etc.). The main packaging 20 may be constructed of various types of materials such as, but not limited to, cardboard, paperboard, plastic and the like.

As illustrated in FIG. 1, the main packaging 20 preferably includes a window 22 within a front portion of the main packaging 20. The window 22 is at least semi-transparent to provide viewing of the interior cavity of the main packaging 20. The window 22 may be an opening or a semi-transparent to transparent sheet of material (e.g. clear plastic).

As further illustrated in FIG. 1, the main packaging 20 preferably includes a support portion 24 and a receiver aperture 26 extending through the support portion 24. The receiver aperture 26 is formed for attaching the main packaging 20 to a store shelf rod or a hook for presentation to consumers for purchase.

C. Fruit.

The fruit 12 used with the fruit 12 and clove pomander kit 10 may be provided within the kit or purchased separately by the end user. If the fruit 12 is included in the fruit 12 and clove pomander kit 10, the fruit 12 may be packaged in its own separate packaging away from the other components of the kit 10. The fruit 12 is preferably spherical shaped, but may have various other types of shape. Examples of suitable fruits 12 for usage in the present invention include, but are not limited to, oranges, apples, lemons, pears, limes, grapefruit 12 and the like.

D. Items Inserted Into Fruit.

Figure 2:
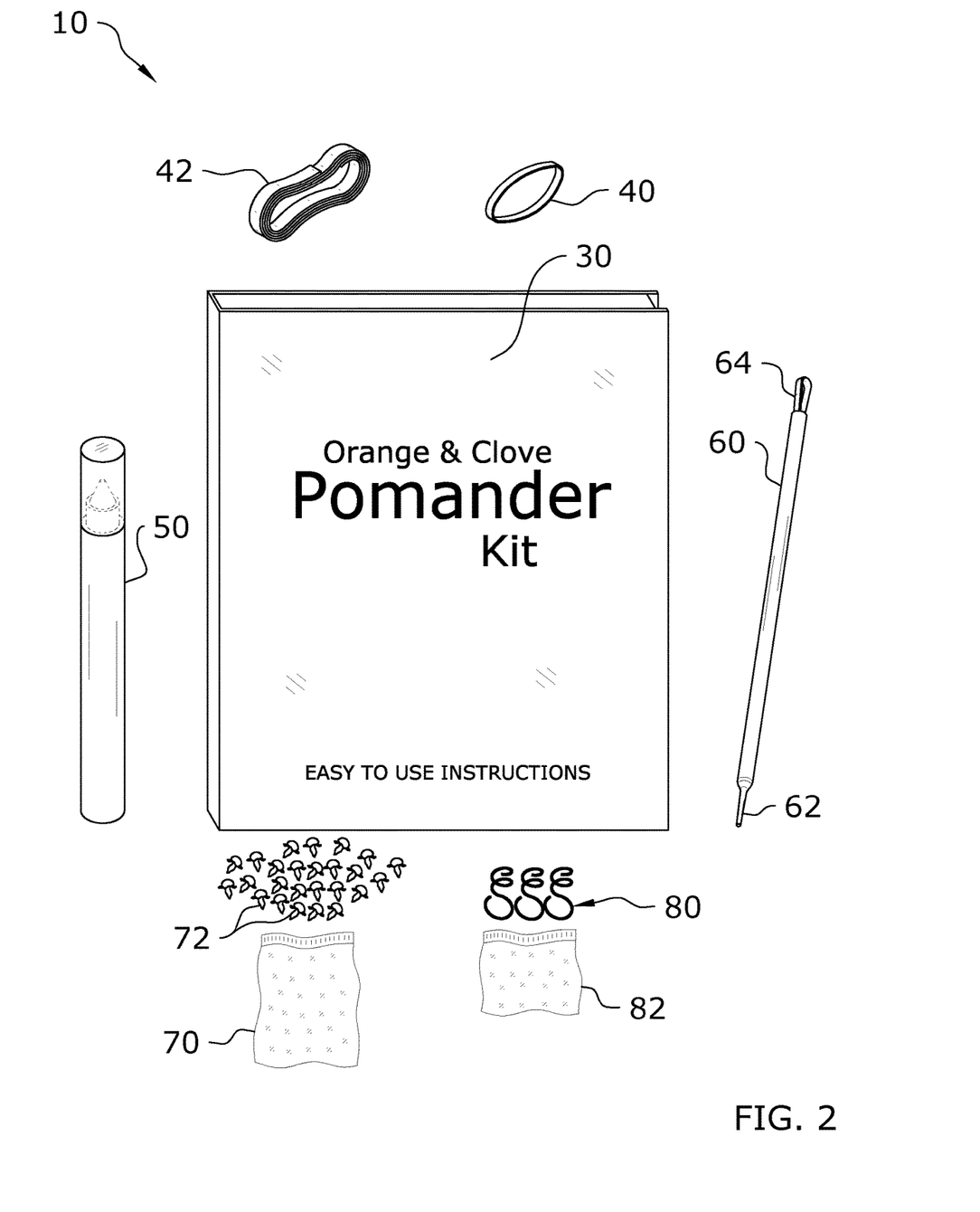
FIG. 2 is an upper perspective view of the present invention.

The kit 10 further includes a plurality of spices and preferably includes a plurality of dried cloves 70 which provide a pleasant scent. The dried cloves 70 are positioned within a clove packaging 72 such as a clear plastic packaging as illustrated in FIGS. 1 and 2. The dried cloves 70 are each comprised of an elongated calyx that terminates in four spreading sepals and four unopened petals that form a small central ball. The dried cloves 70 are each preferably approximately 1.5 cm to 2.0 cm in length. The elongated portion of the dried cloves 70 opposite of the sepals and petals is inserted into exterior surface of the fruit 12.

The present invention may utilize various other types of spices that provide a pleasant scent such as cinnamon, rosemary, anise, mint, sage, licorice and the like. The present invention may also have other types of items inserted into the pierced holes 16 of the fruit 12 such as, but not limited to, flowers or plants (e.g. chamomile, baby's breath, eucalyptus, pine, cedar), edible and non-edible berries (e.g. cranberries, holly hush berries, nandina bush berries), incense sticks or cones, cinnamon toothpicks and other items that have a pleasant smell to individuals. Cinnamon toothpicks may also be used in combination with other items or for securing other items (e.g. berries) to the fruit 12. Various combinations of items may be inserted into the fruit 12 (e.g. dried cloves 70 may be inserted along with mint).

E. Carving and Piercing Tool.

The kit 10 further includes a carving and piercing tool 60 as illustrated in FIGS. 1 and 2. The carving and piercing tool 60 includes a piercing end 62 adapted to create pierced holes 16 within a fruit 12 and a carving end 64 opposite of the piercing end 62 as illustrated in FIGS. 4a through 4f of the drawings. The carving and piercing tool 60 is illustrated as a single tool structure with an elongated handle portion between the piercing end 62 and the carving end 64. However, the carving and piercing tool 60 may be comprised of two separate tools with one tool having a handle with a piercing end 62 and the second tool having a handle with the carving end 64.

The carving end 64 of the carving and piercing tool 60 is adapted to carve a channel 14 within a layer of skin of the fruit 12. The carving end 64 is preferably comprised of a looped structure having opposing bladed edges as illustrated in FIGS. 4a, 4b, 4c and 4f of the drawings. The looped structure of the carving end 64 is preferably an elongated loop with a curved end that is shaped to form a desired curvature for the channel 14. Various widths and radius of curvature may be used for the end of the elongated loop to create various depths, widths and shapes of channels 14 within the fruit 12.

Figure 4A:
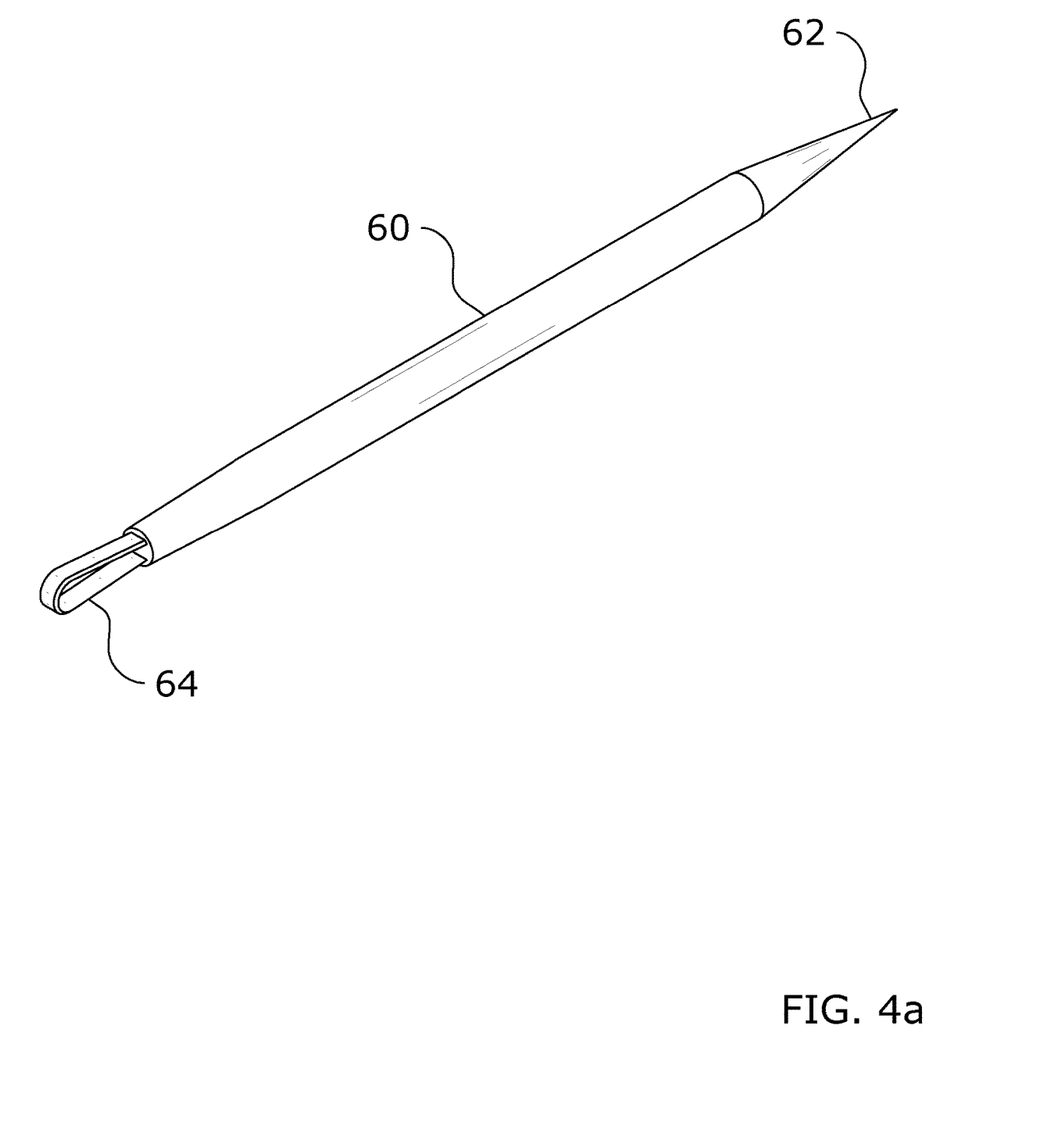
FIG. 4a is a first perspective view of the carving and piercing tool.
Figure 4B:
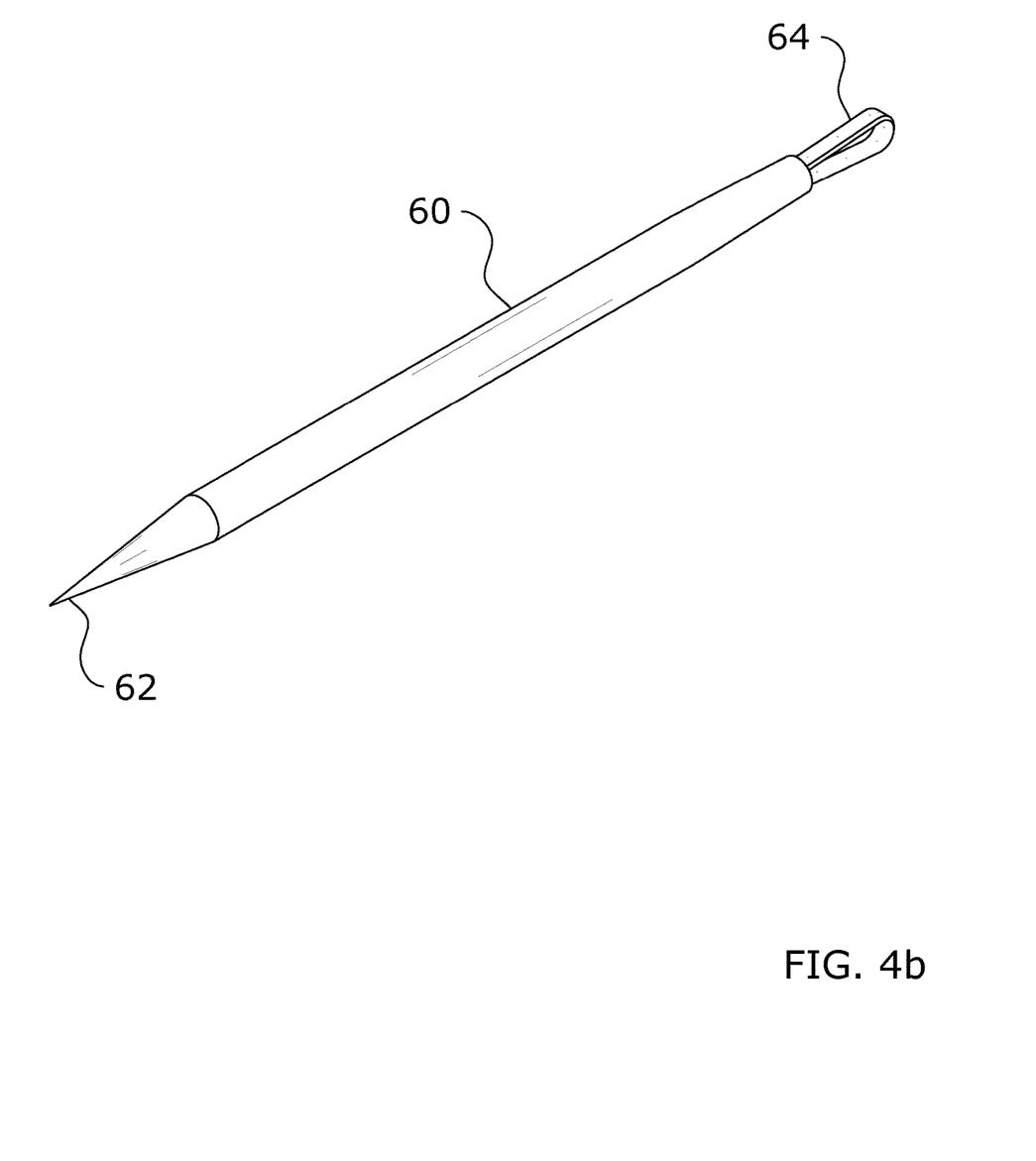
FIG. 4b is a second perspective view of the carving and piercing tool.
Figure 4C:
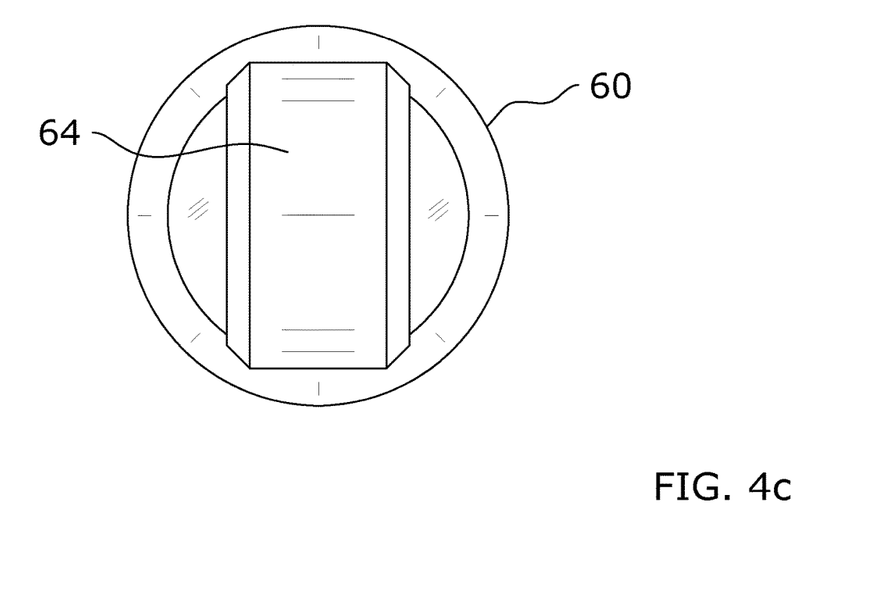
FIG. 4c is a first end view of the carving and piercing tool showing the carving end.
Figure 4D:
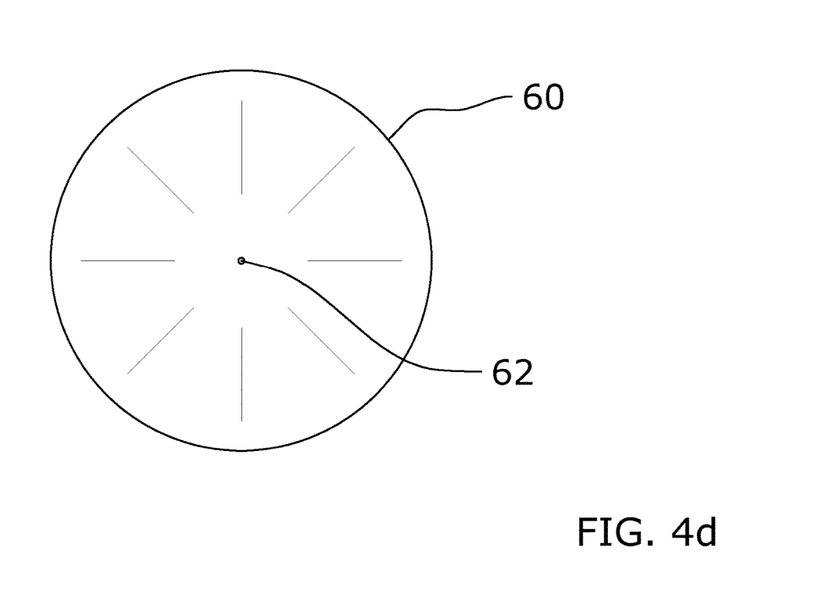
FIG. 4d is a second end view of the carving and piercing tool showing the piercing end.
Figure 4E:
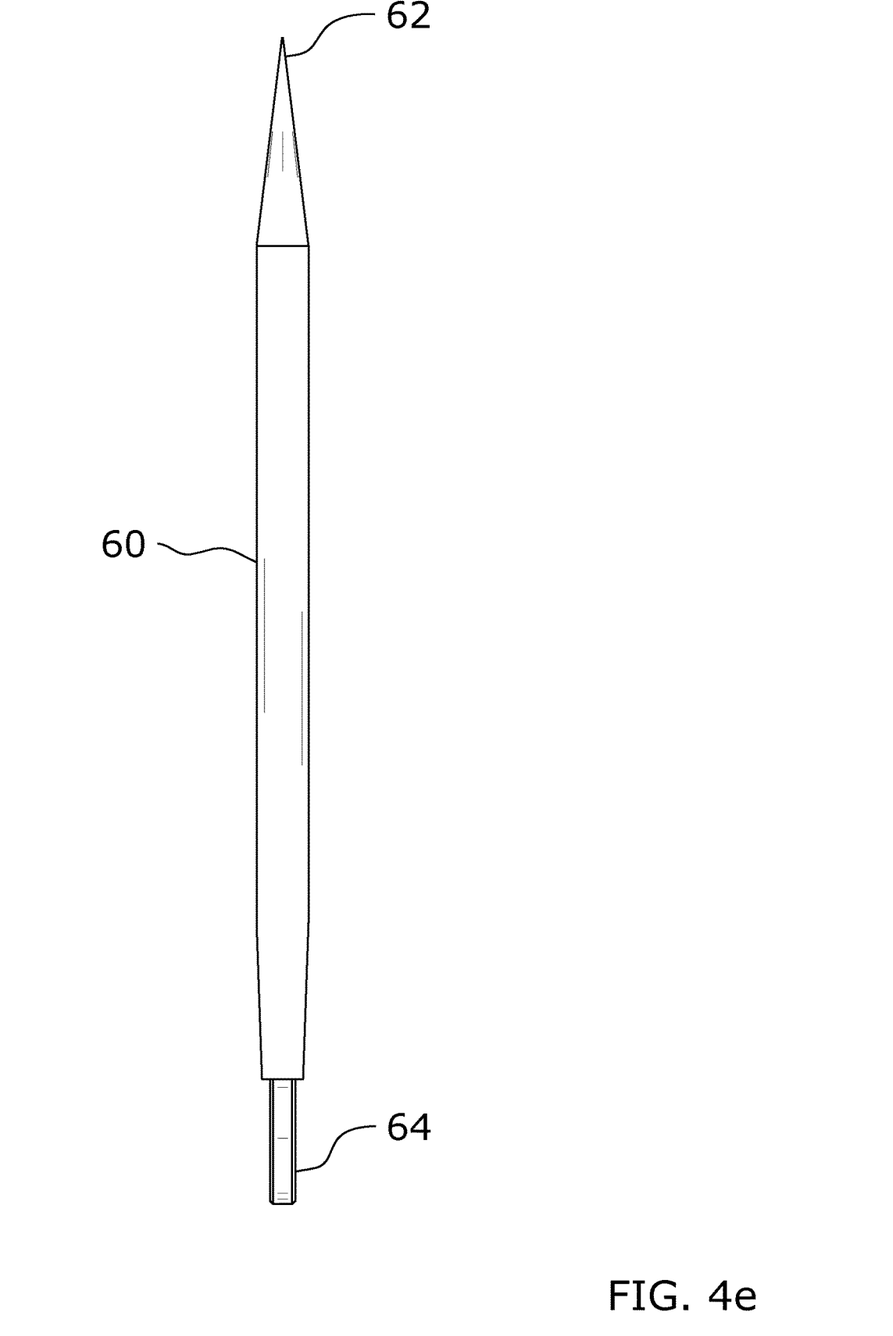
FIG. 4e is a side view of the carving and piercing tool.
Figure 4F:
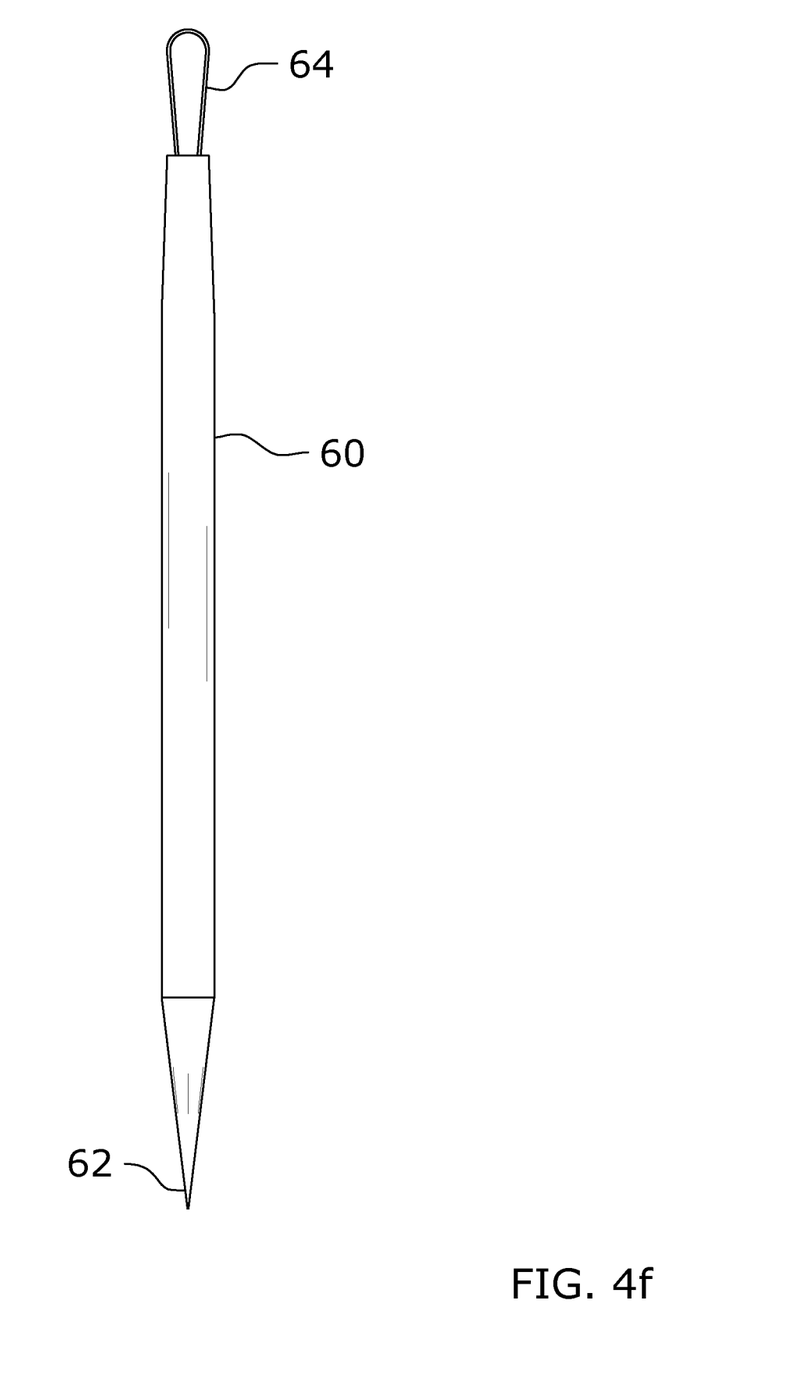
FIG. 4f is a side view of the carving and piercing tool rotated ninety degrees.
Figure 5A:
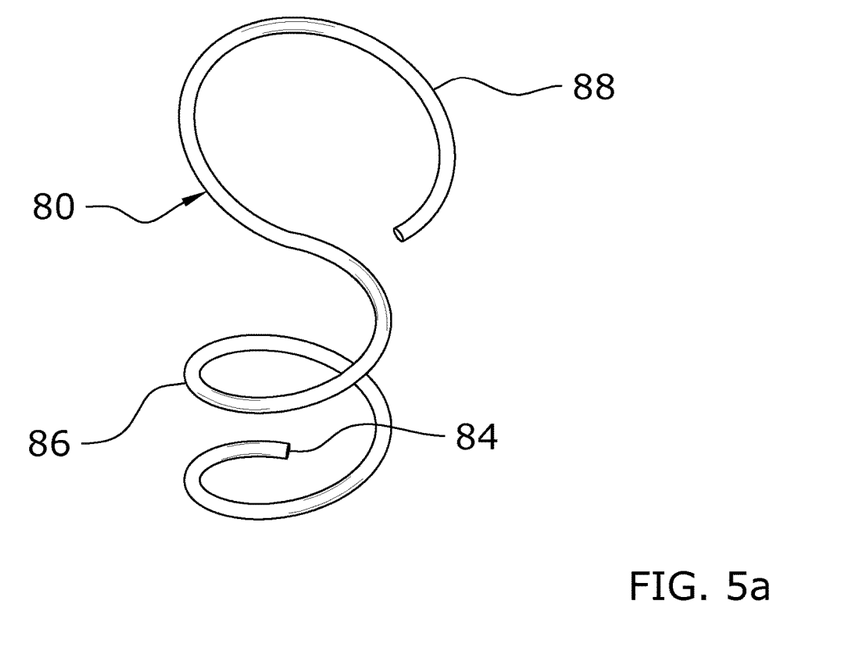
FIG. 5a is an upper perspective view of the hanger hook.
Figure 5B:
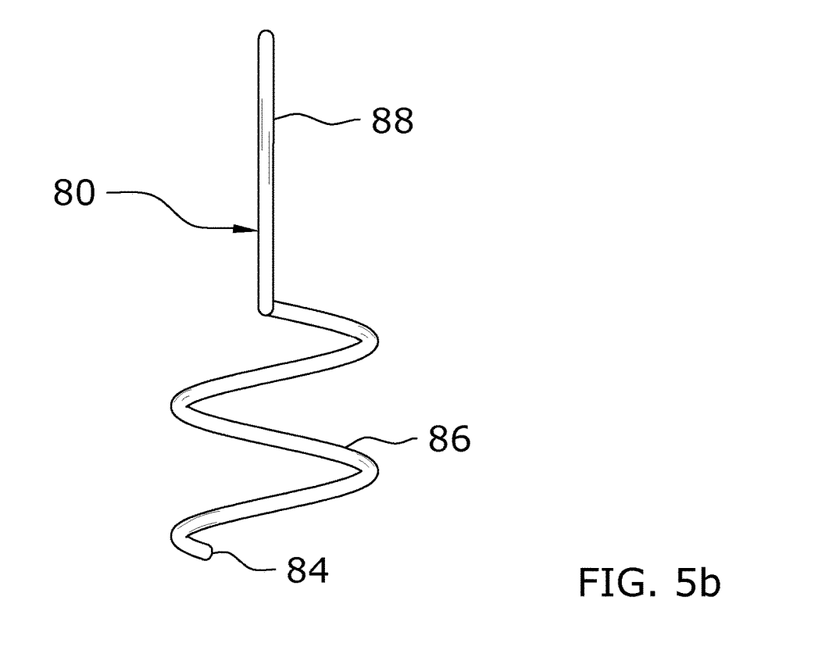
FIG. 5b is a side view of the hanger hook.
Figure 5C:
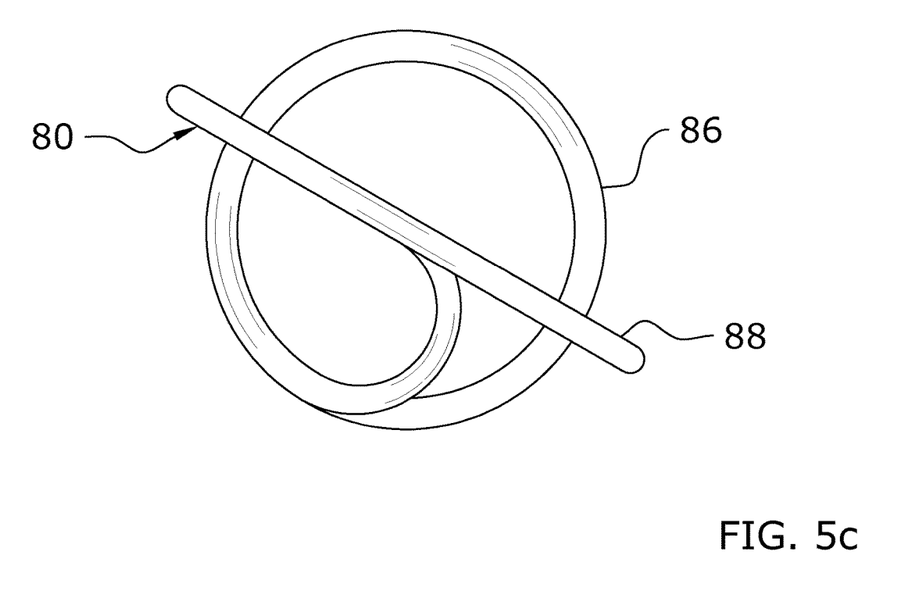
FIG. 5c is a top view of the hanger hook.
Figure 5D:
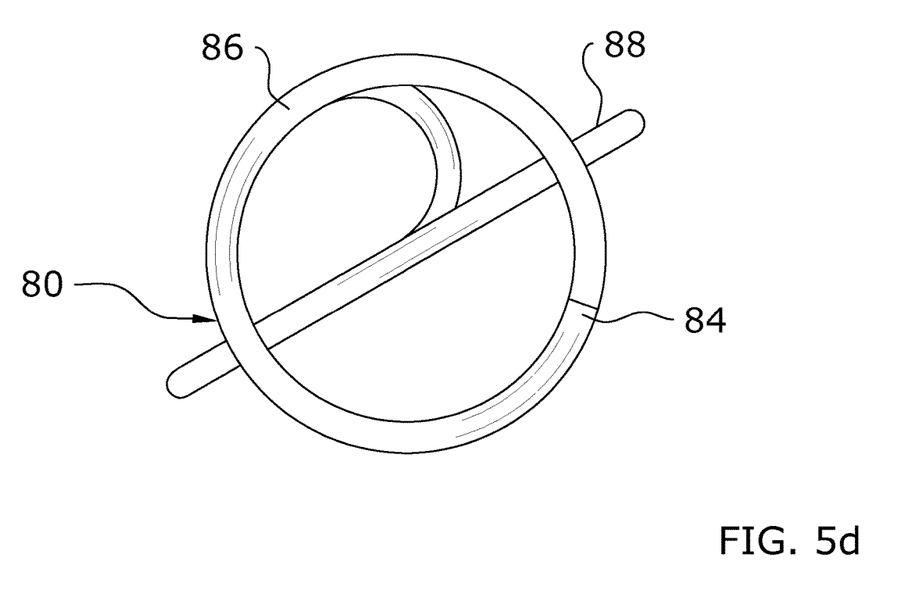
FIG. 5d is a bottom view of the hanger hook.

The piercing end 62 of the carving and piercing tool 60 is comprised of a pointed and tapered structure as best illustrated in FIG. 4e of the drawings. The piercing end 62 of the carving and piercing tool 60 is adapted to pierce the skin of various types of fruit 12 to create a plurality of pierced holes 16 in the exterior surface of the fruit 12 to allow for insertion of the dried cloves 70. The pierced hole 16 created by the piercing end 62 of the carving and piercing tool 60 preferably tapers from a broader opening on the outer surface of the fruit 12 to a narrower opening within the inner portion of the fruit 12 thereby creating an entry opening sufficient in size to receive the end of the elongated portion of the dried clove 70 and a narrower lumen inside of the fruit 12 to frictionally retain the dried clove 70 within the fruit 12 after insertion.

F. Rubber Band.

Figure 3A:
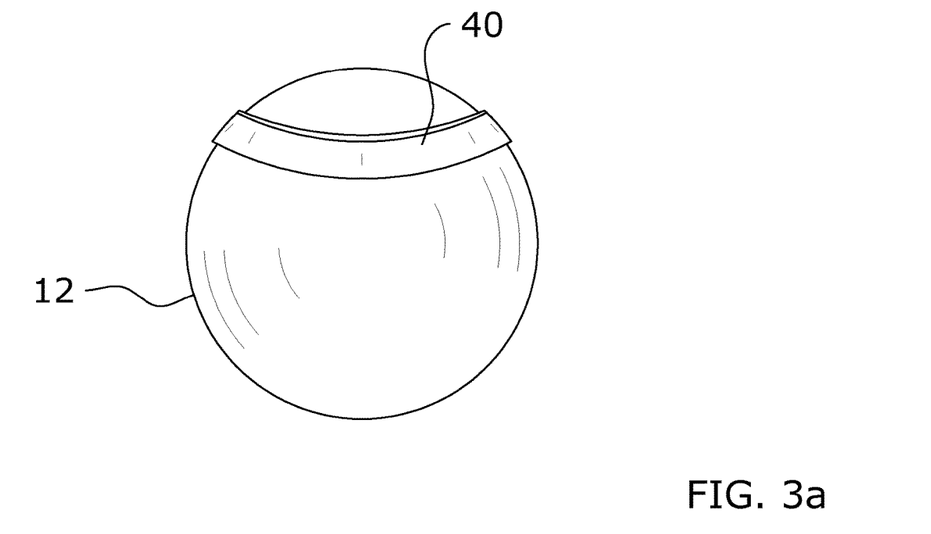
FIG. 3a is a perspective view of a rubber band attached to a portion of the fruit.
Figure 3B:
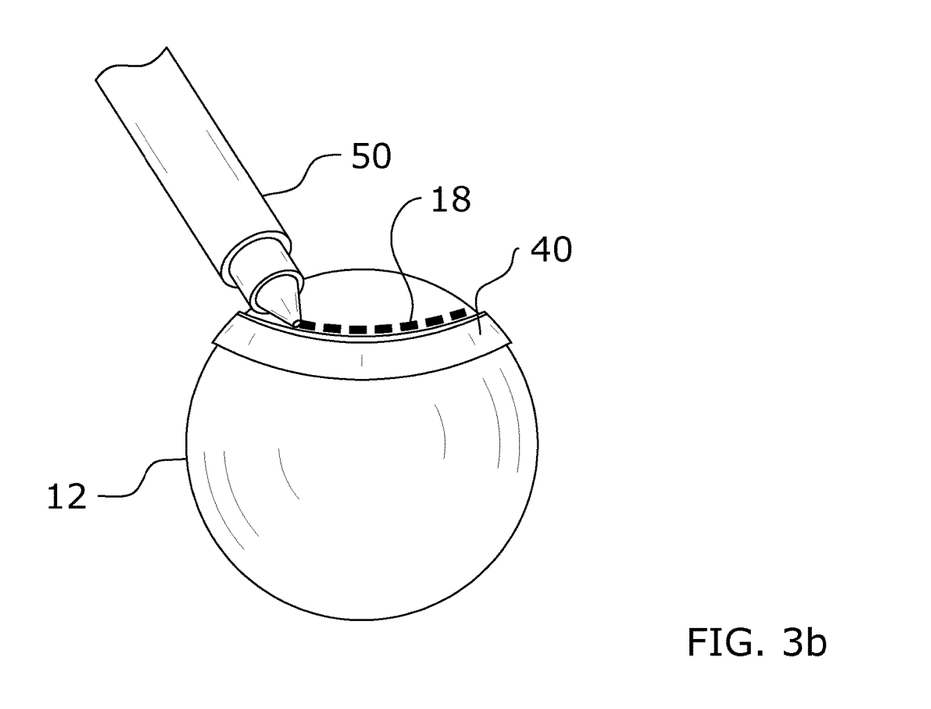
FIG. 3b is a perspective view of a writing instrument drawing an indicia line adjacent to the edge of the rubber band.

The kit 10 also includes at least one rubber band 40. The rubber band 40 is comprised of an elastic material (e.g. synthetic rubber) that is formed into a closed loop suitable for attaching to an exterior surface of the fruit 12 as illustrated in FIGS. 3a and 3b of the drawings. The rubber band 40 may be comprised of any elastic band suitable for removably attaching to the exterior surface of the fruit 12.

G. Writing Instrument.

The kit 10 further includes at least one writing instrument 50 used to write upon the exterior surface of the fruit 12 to provide alignment markings on the fruit 12 indicating where to pierce holes and carve channels 14. The writing instrument 50 may be comprised of various devices capable of writing on an object such as, but not limited to, a pen, a marker and the like. The ink used by the writing instrument 50 may be black or colored.

H. Hanger Hook.

The kit 10 further includes at least one hanger hook 80 that is inserted into the upper end of the fruit 12. The hanger hook 80 is constructed of a narrow structure such as metal wire. The hanger hook 80 is comprised of a helical portion 86, an engaging portion 88 extending upwardly from the helical portion 86 and an end portion 84 extending downwardly from the helical portion 86 opposite of the engaging portion 88 as illustrated in FIGS. 5a through 5d of the drawings.

The engaging portion 88 of the hanger hook 80 is comprised of an open looped structure or a closed loop structure adapted for connecting to a ribbon 42 or hook to support the completed pomander in a desired location. The end portion 84 of the hanger hook 80 is comprised of a pointed end to pierce and penetrate the skin of the fruit 12.

Figure 3C:
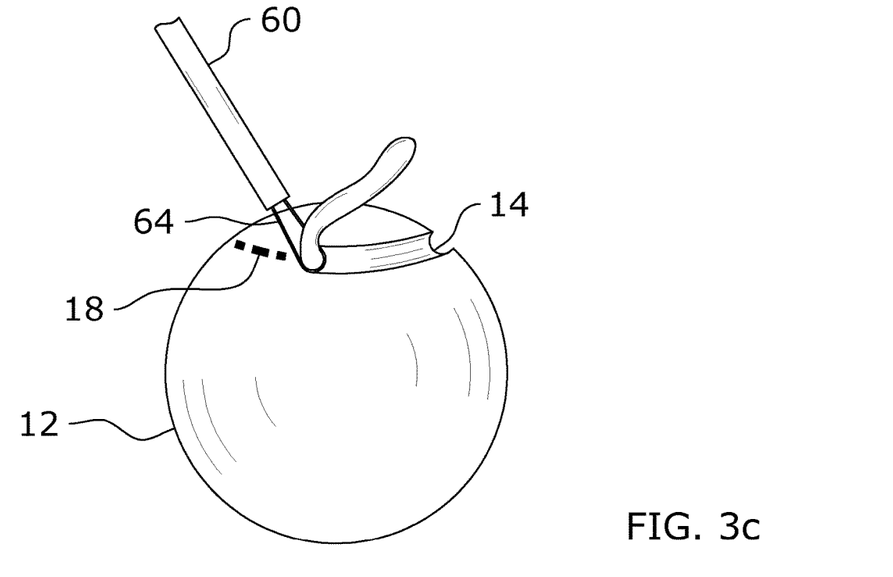
FIG. 3c is a perspective view of the carving and piercing tool creating a channel in the skin of the fruit along the indicia line.
Figure 3D:
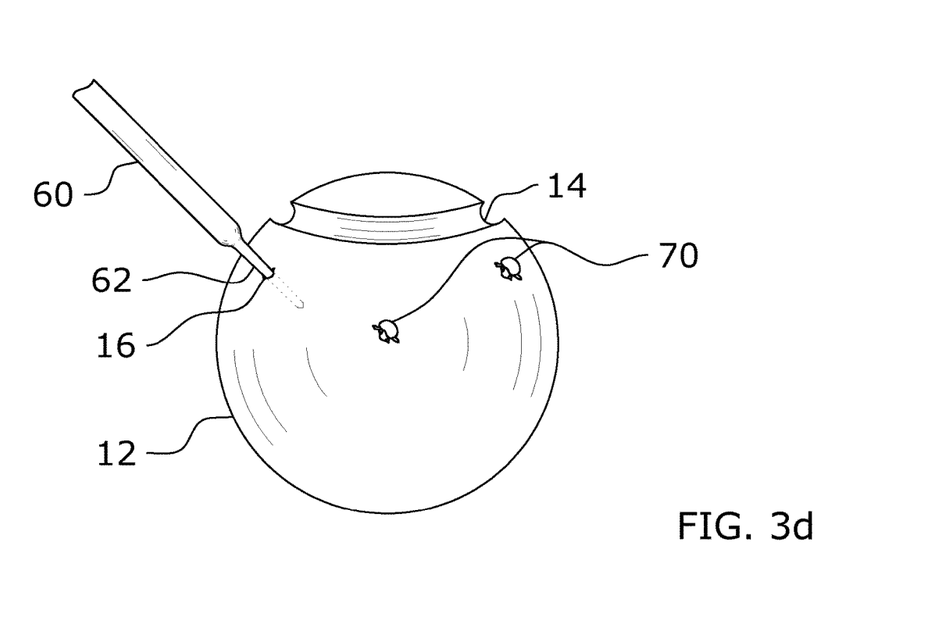
FIG. 3d is a perspective view of the carving and piercing tool creating pierced holes in the fruit for allowing insertion of a dried clove.
Figure 3E:
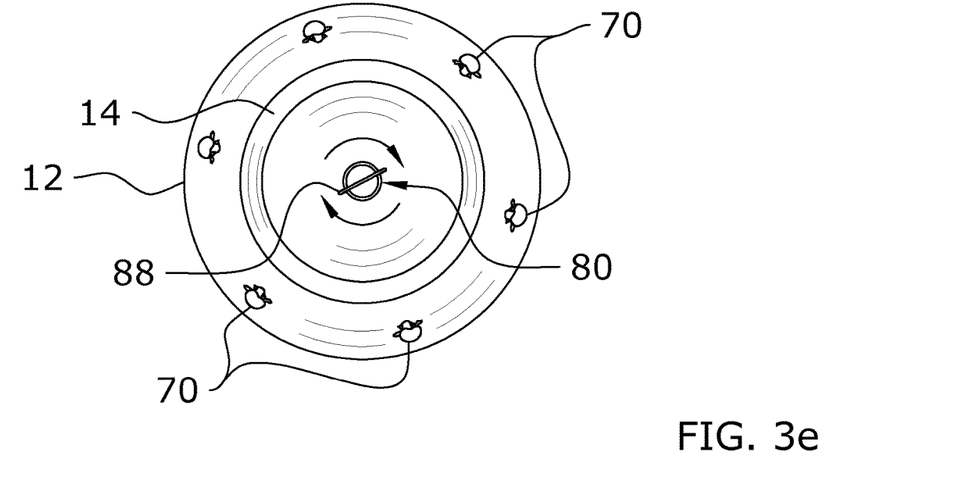
FIG. 3e is a top view of a hanger hook being screwed into the top of the fruit.
Figure 3F:
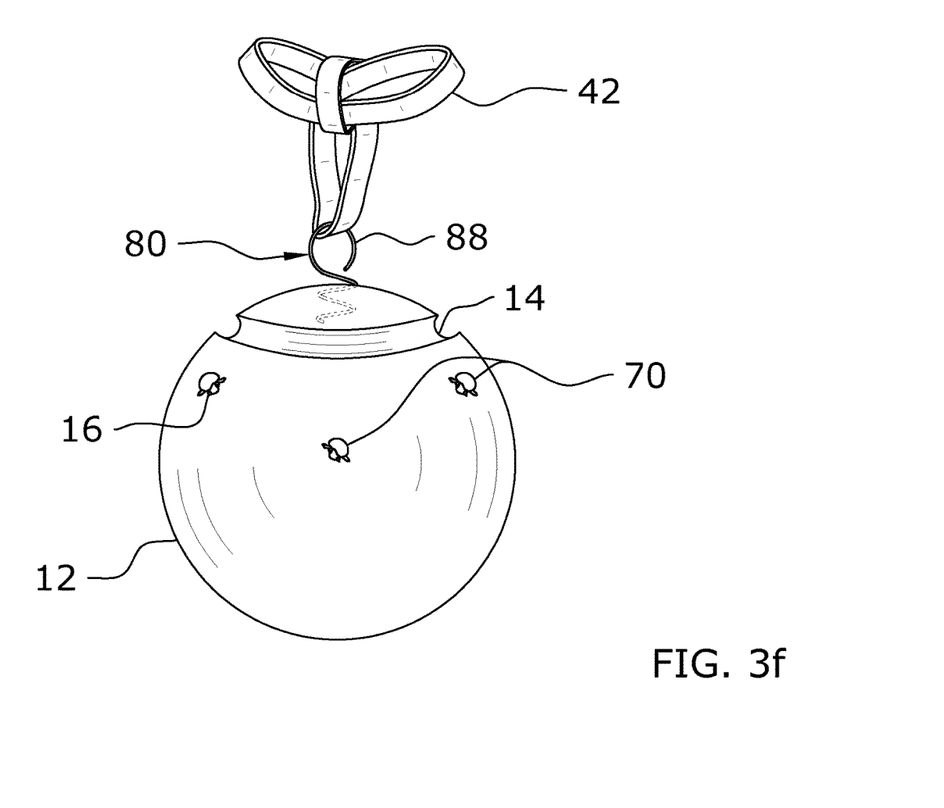
FIG. 3f is a perspective view of the completed fruit and clove pomander.

The user rotates the hanger hook 80 with respect to the fruit 12 wherein the helical portion 86 drives the hanger hook 80 into the fruit 12 until only the engaging portion 88 is exposed from the fruit 12 as illustrated in FIG. 3f of the drawings. A plurality of hanger hooks 80 are included in the kit 10 and are stored within a separate hanger packaging 82 comprised of a clear plastic material.

I. Ribbon.

The kit 10 further includes at least one ribbon 42. The ribbon 42 may be comprised of any elongated thin band of material (e.g. cloth, plastic) which may be used to attach to the hanger hook 80 inserted into the fruit 12 as illustrated in FIG. 3f of the drawings. The ribbon 42 is used for decorative purposes and also for functionally hanging the completed pomander in a desired location. The ribbon 42 is tied to the hanger hook 80 or secured with a fastener to the hanger hook 80. The ribbon 42 may be colored and have various translucencies.

J. Instruction Book.

The kit 10 further includes an instruction book 30 positioned within the interior cavity of the main packaging 20. The instruction book 30 provides guidance and instructions on how to create a fruit 12 and clove pomander. The instruction book 30 also provides examples and illustrations for designs to use in creating a fruit 12 and clove pomander. The instruction book 30 also includes patterns and templates that may be positioned upon the fruit 12 to use in creating piercing patterns for creating a plurality of pierced holes 16 in a desired pattern (e.g. star shape pattern, angled parallel lines, etc.) which the user inserts the piercing end 62 through at the marked locations on the pattern sheet.

K. Operation of Preferred Embodiment.

To use the kit 10, the desired fruit 12 (e.g. an orange) is provided either in the kit 10 or purchased separately by the end user. The user then attaches the rubber band 40 to the fruit 12 in a desired location to form a channel 14 as illustrated in FIG. 3a of the drawings. The user then draws an indicia line 18 on an exterior surface of the fruit 12 adjacent to the rubber band 40 with the writing instrument 50 to mark the location for the channel 14. The user repositions the rubber band 40 and draws additional indicia lines 18 if additional channels 14 are desired. The user then removes the rubber band 40 from the fruit 12 and carves a channel 14 into in the exterior surface of the fruit 12 along the indicia line 18 with the carving end 64 of the carving and piercing tool 60 as illustrated in FIG. 3c of the drawings. The carving end 64 forms a desired channel 14 which may extend around the entire perimeter of the fruit 12 as illustrated in FIG. 3e of the drawings or only a portion of the fruit 12.

The user then marks on the exterior surface of the fruit 12 the desired locations of the pierced holes 16 where the dried cloves 70 will be inserted into. The marks may be added free hand or using a template. The user then pierces the plurality of pierced holes 16 within the exterior surface of the fruit 12 with the piercing end 62 of the carving and piercing tool 60 as illustrated in FIG. 3d of the drawings. After the pierced holes 16 are formed within the fruit 12, the user then inserts the plurality of dried cloves 70 into the plurality of pierced holes 16 as illustrated in FIG. 3d of the drawings.

After the fruit 12 has had the channels 14 carved and the dried cloves 70 attached to the exterior surface of the fruit 12, the user then attaches the hanger hook 80 into an upper portion of the fruit 12 with the engaging portion 88 exposed outside of the exterior surface. The user attaches the hanger hook 80 by screwing the hanger hook 80 into the fruit 12 with the end portion 84 piercing the fruit 12 and the helical portion 86 drawing the hanger hook 80 into the fruit 12 as illustrated in FIG. 3e of the drawings. The user continues to screw the hanger hook 80 into the fruit 12 until only the engaging portion 88 is exposed outside of the fruit 12 as illustrated in FIG. 3f of the drawings.

After the hanger hook 80 is properly attached to the fruit 12, the user then attaches a ribbon 42 or hook to the engaging portion 88 of the hanger hook 80 for use in removably attaching the completed fruit 12 and clove pomander to an object (e.g. a tree, a door knob, a hook, etc.). The user may also dry the completed fruit 12 and clove pomander prior to usage.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A method of using a fruit and clove pomander system, comprising:
   providing a fruit;
   attaching a rubber band to said fruit;
   drawing an indicia line on an exterior surface of said fruit adjacent to said rubber band;
   removing said rubber band;
   providing a carving and piercing tool comprising a piercing end and a carving end;
   carving a channel within said exterior surface of said fruit along said indicia line with said carving end of said carving and piercing tool;
   piercing a plurality of pierced holes within said exterior surface of said fruit with said piercing end of said carving and piercing tool;
   inserting a plurality of dried cloves into said plurality of pierced holes;
   providing a hanger hook comprised of a helical portion, an engaging portion extending upwardly from said helical portion and an end portion extending downwardly from said helical portion opposite of said engaging portion, wherein said engaging portion is comprised of an open looped structure or a closed loop structure adapted for connecting to a ribbon or hook, wherein said end portion is comprised of a pointed end; and
   screwing said hanger hook into an upper portion of said fruit with said engaging portion exposed outside of said exterior surface.

2. The method of claim 1, including attaching a ribbon or hook to said engaging portion of said hanger hook.

* * * * *